United States Patent
Catt et al.

(10) Patent No.: US 6,234,974 B1
(45) Date of Patent: May 22, 2001

(54) MONITORING METHOD

(75) Inventors: Michael Catt, Wellingborough; John Coley, Stanwick; Paul J Davis, Felmersham, all of (GB)

(73) Assignee: Unilever Patent Holdings B.V., Bedford (GB)

( * ) Notice: Subject to any disclaimer, the term of this patent is extended or adjusted under 35 U.S.C. 154(b) by 0 days.

(21) Appl. No.: 08/772,522

(22) Filed: Dec. 24, 1996

Related U.S. Application Data (60) Continuation of application No. 08/525,371, filed on Sep. 7, 1995, now abandoned, which is a division of application No. 08/109,503, filed on Aug. 20, 1993, now Pat. No. 5,467,778.

(30) Foreign Application Priority Data

Aug. 21, 1992 (GB) .................................................. 9217864

(51) Int. Cl.[7] .................................................. A61B 10/00

(52) U.S. Cl. ........................................................... 600/551

(58) Field of Search .............................. 436/65; 435/7.95; 361/413.12; 600/551

(56) References Cited

U.S. PATENT DOCUMENTS

| | | |
|---|---|---|
| 3,141,740 | 7/1964 | Wild . |
| 3,406,015 | 10/1968 | Foster . |
| 3,406,016 | 10/1968 | Foster et al. . |
| 3,434,801 | 3/1969 | Scherr . |
| 3,436,186 | 4/1969 | Mcsweeney et al. . |
| 3,749,089 | 7/1973 | Derr . |
| 3,875,013 | 4/1975 | Manautou et al. . |
| 3,924,609 | 12/1975 | Friedenberg et al. . |
| 3,926,037 | 12/1975 | Kopito et al. . |

(List continued on next page.)

FOREIGN PATENT DOCUMENTS

| | | |
|---|---|---|
| 1 048 001 | * 2/1979 | (CA) . |
| 1 183 080 | * 2/1985 | (CA) . |
| 1 214 438 | * 4/1966 | (DE) . |

(List continued on next page.)

OTHER PUBLICATIONS

Billings et al; "Symptons and hormonal changes accompanying ovulation"; The Lancett; 2–1972; pp. 282–284.
Collins, Intl., J. Gynecology and Obstetrics, Suppl., No. 1, pp. 35–43 (1989).
Cekan et al, Contraception, 33(4): 327–345 (1986).
Bischof et al, Human Reproduction, 6(4): 515–518 (1991).
Brown et al, Intl J. Gynecology and Obstetrics, Suppl. No. 1, pp 111–122 (1989).

(List continued on next page.)

*Primary Examiner*—John P. Lacyk
*Assistant Examiner*—Pamela L. Wingood
(74) *Attorney, Agent, or Firm*—Pillsbury Madison & Sutro LLP (57) ABSTRACT

A method of monitoring the status of a current ovulation cycle of an individual human female subject, involving testing of the body fluid concentration of an analyte of significance in relation to the status of the ovulation cycle, such as urinary E3G, during at least part of the pre-ovulation phase of the current ovulation cycle of the individual subject, and identification from the results of such testing an analyte concentration change indicative of imminent ovulation, relative to an analyte concentration reference value that has been adapted to the individual human subject on the basis of analyte concentration test data obtained from the individual human subject during one or more previous ovulation cycles. Preferably testing for said analyte concentration during the current ovulation cycle is commenced a plurality of days (preferably at least 5) following the onset of menses but at least 2 numerical days in advance of the earliest numerical day on which actual ovulation has occurred in one or more previous ovulation cycles in the same individual subject.

13 Claims, 2 Drawing Sheets

U.S. PATENT DOCUMENTS

| | | |
|---|---|---|
| 3,968,011 | 7/1976 | Manautou et al. . |
| 3,986,494 | 10/1976 | Preti et al. . |
| 3,991,174 | 11/1976 | Grundman . |
| 4,002,056 | 1/1977 | Kopito et al. . |
| 4,010,738 | 3/1977 | Preti et al. . |
| 4,013,066 | 3/1977 | Schuster . |
| 4,031,365 | 6/1977 | Raggiotti et al. . |
| 4,036,212 | 7/1977 | Karuhn . |
| 4,059,986 | 11/1977 | Schuster . |
| 4,072,045 | 2/1978 | Kopito . |
| 4,119,089 | 10/1978 | Preti et al. . |
| 4,123,510 | 10/1978 | Banik et al. . |
| 4,148,304 | 4/1979 | Mull . |
| 4,151,831 | 5/1979 | Lester . |
| 4,151,833 | 5/1979 | Polishuk . |
| 4,208,187 | 6/1980 | Givner . |
| 4,232,215 | 11/1980 | Hanley . |
| 4,246,907 | 1/1981 | Bullock . |
| 4,261,371 | 4/1981 | Reading, III . |
| 4,312,360 | 1/1982 | Conway et al. . |
| 4,367,527 | 1/1983 | Desjacques . |
| 4,370,727 | 1/1983 | Bellet . |
| 4,377,171 | 3/1983 | Wada . |
| 4,381,121 | 4/1983 | Hanley . |
| 4,385,125 | 5/1983 | Preti et al. . |
| 4,396,020 | 8/1983 | Wolff et al. . |
| 4,408,905 | 10/1983 | Ehrenkranz . |
| 4,443,851 | 4/1984 | Lin . |
| 4,450,239 | 5/1984 | Chatterton . |
| 4,465,077 | 8/1984 | Schneider . |
| 4,466,445 | 8/1984 | Abrams . |
| 4,475,158 | 10/1984 | Elias . |
| 4,488,560 | 12/1984 | Takamura . |
| 4,498,481 * | 2/1985 | Lemke . |
| 4,530,366 * | 7/1985 | Nessi et al. . |
| 4,534,362 * | 8/1985 | Schumacher et al. . |
| 4,557,273 * | 12/1985 | Stoller et al. . |
| 4,614,715 * | 9/1986 | Tsibris et al. . |
| 4,670,401 * | 6/1987 | Cutler et al. . |
| 4,676,254 | 6/1987 | Frohn . |
| 4,685,471 * | 8/1987 | Regas et al. . |
| 4,691,714 * | 9/1987 | Wong et al. . |
| 4,752,880 * | 6/1988 | Aeschlimann . |
| 4,753,247 * | 6/1988 | Kirsner . |
| 4,770,186 * | 9/1988 | Regas et al. . |
| 4,779,627 * | 10/1988 | Kosasky . |
| 4,788,984 * | 12/1988 | Marsik . |
| 4,921,808 * | 5/1990 | Schneyer et al. . |
| 5,043,888 * | 8/1991 | Uriarte . |
| 5,050,612 | 9/1991 | Matsumura . |
| 5,063,903 | 11/1991 | Nucci . |
| 5,091,170 | 2/1992 | Navot . |
| 5,118,630 | 6/1992 | Glaze . |
| 5,120,660 * | 6/1992 | Kuniyuki . |
| 5,137,028 | 8/1992 | Nishimura . |
| 5,209,238 | 5/1993 | Sundhar . |
| 5,216,599 | 6/1993 | Uebe et al. . |
| 5,242,804 * | 9/1993 | Banar et al. ......... 435/7.93 |
| 5,248,593 | 9/1993 | Hubner-Parajsz et al. . |

FOREIGN PATENT DOCUMENTS

| | | |
|---|---|---|
| 28 03 152 * | 7/1979 | (DE) . |
| 28 47 397 * | 5/1980 | (DE) . |
| 3 037 977 * | 5/1982 | (DE) . |
| 3 221 999 * | 4/1983 | (DE) . |
| 3 247 750 | 6/1984 | (DE) . |
| 3 314 442 | 11/1984 | (DE) . |
| 3 325 598 | 1/1985 | (DE) . |
| 3 342 251 | 5/1985 | (DE) . |
| 3 343 020 | 6/1985 | (DE) . |
| 3 528 964 | 2/1987 | (DE) . |
| 3 609 956 | 10/1987 | (DE) . |
| 3 802 479 | 8/1989 | (DE) . |
| 0 097 851 | 6/1983 | (EP) . |
| 0 132 199 | 7/1984 | (EP) . |
| 0 011 594 | 12/1984 | (EP) . |
| 0 195 207 | 1/1986 | (EP) . |
| 0 225 054 | 10/1986 | (EP) . |
| 0 286 743 | 4/1987 | (EP) . |
| 0 339 092 | 12/1987 | (EP) . |
| 0 291 194 | 4/1988 | (EP) . |
| 0291194 | 11/1988 | (EP) . |
| 0 367 615 | 11/1989 | (EP) . |
| 0 177 994 | 1/1990 | (EP) . |
| 0 383 619 | 2/1990 | (EP) . |
| 0 385 621 | 2/1990 | (EP) . |
| 0367615 | 5/1990 | (EP) . |
| 0 424 102 | 10/1990 | (EP) . |
| 0 470 507 | 8/1991 | (EP) . |
| 0 476 703 | 9/1991 | (EP) . |
| 0 498 303 | 1/1992 | (EP) . |
| 0 653 625 | 11/1994 | (EP) . |
| 2 290 876 * | 6/1976 | (FR) . |
| 2305161 | 11/1976 | (FR) . |
| 2 652 092 * | 3/1991 | (FR) . |
| 945670 | 1/1964 | (GB) . |
| 1 203 619 | 8/1970 | (GB) . |
| 2 045 480 | 10/1980 | (GB) . |
| 2 106 646 | 4/1983 | (GB) . |
| 2 116 318 * | 9/1983 | (GB) . |
| 2 186 977 | 8/1987 | (GB) . |
| WO 80/02800 | 12/1980 | (WO) . |
| WO 84/03381 | 8/1984 | (WO) . |
| WO 87/02774 | 5/1987 | (WO) . |
| WO 90/11521 | 10/1990 | (WO) . |
| WO 91/15594 | 10/1991 | (WO) . |
| WO 94/02850 | 2/1994 | (WO) . |
| WO 94/04926 | 3/1994 | (WO) . |
| WO 95/16920 | 6/1995 | (WO) . |

OTHER PUBLICATIONS

Djerassi, Science, 248:1061–1062 (1990).

Vermesh et al, Fertility and Sterility, 47(2): 259–264 (1987).

Schiphorst et al, Fertility and Sterility, 44(3): 328–334 (1985).

Judge et al, Steroids, 31(2):175–187 (1978).

World Health Organization Task Force, Intl., J. of Fertility, 30(3): 18–30 (1985).

Adlercreutz et al., "Prediction of ovulation by urinary estrogen assays", J. Steroid Biochem, 1980, v.12, pp 395–348.

Adlercreutz et al., "The measurement of urinary steroid glucuronides as indices of the fertile period in women", J. Steroid Biochem, 1982, v. 17, pp 695,702.

Albertson et al., "Review Article: The prediction of ovulation and monitoring of the fertile period", Adv. Contracept, v. 3, pp 263–290.

Baird et al., "Using the ratio of urinary oestrogena nd progesterone metabolites to estimate day of ovulation", Statistics in Medicine, 1991, 10, pp 255–266.

Barnard et al., "A nonseparation, time–resolved fluoroimmunoassay to minitor ovarian function and predict potential infertility in women", Fertility and Sterility, 1989, 52(1), pp 60–65.

Bieglmayer et al., "Evaluation of a simple and fast self–test for urine luteinizing hormone", Fertility and Sterility, 1990, 53(5), pp 842–846.

Bischof et al., "Comparison of a rapid, quantitative and automated assay for urinary luteinizing hormone (LH), with an LH detection test, for the prediction of ovulation", Human Reproduction, 1991, 6(4), pp 515–518.
Bonnar, "Biological methods of identifying the fertile period", Fertility and Sterility, 1984, Eds. Harrison et al., MTP Press, pp 77–92.
Brown et al., "Appendix 1: Correlations between the mucus symptoms and the hormone markers of fertility throughout reproductive life", The Ovulation Method, 7$^{th}$ Ed., Ed. Bilings, Advocate Press, Melbourne, 1983, pp 99–125.
Brown et al., "Natural Family Planning", Am. J. Obstet. Gynecol, 1987, 157(4), Part 2, pp 1082–1089.
Brown et al., "Chemical and homogeneous immunoassay methods for the measurement of estrogens and pregnanediol and their glucuronides in urine", Non–Radiometric Assays: Technology and Application in Polypeptide and Steroid Hormone Detection, Publ. Alan R. Liss, Inc., 1988, pp 119–138.
Burger, "The physiologica basis of the fertile period", Fertility and Sterility, Eds. Harrison et al., MTP Press, 1984, pp. 51–58.
Burger, Estradiol: the physiological basis of the fertile period:, Int. J. Gynecol Obstet, Suppl 1, 1989, pp 5–9.
Campbell, "Methods of monitoring ovarian function and predicting ovulation: summary of a meeting", Research Frontiers in Fertility Regulation, 1985, 3(5), pp 1–16.
Cardone et al., "Objective and subjective data for fertile period diagnosis in women: comparison of methods", Clin Exp Obst Gyn, XIX, 1992, 1, pp 15–24.
Cekan et al., "The prediction and/or detection of ovulation by means of urinary steroid assays", Contraception, 1986, 33(4), pp 327–345.
Collins et al., "The concentrations of urinary oestrone–3–glucuronide, LH and pregnanediol–3a–gluronide as indices of ovarian function", Acta Endocrinologia, 1979, 90, pp 336–347.
Collins et al., "Biochemical indices of the fertile period in women", Int J Fertil, 1981, 26(3), pp 196–202.*
Collins et al., "Ovulation prediction and detection by the measurement of steroid glucuronides", Proc X Int Congress on Fertility and Sterility, 1981, pp 19–33.*
Collins et al., "Biochemical methods for predicting ovulation", Fertility and Sterility, 1984, pp 59–69.*
Collins, "Hormonal indices of ovulation and the fertile period", Adv Contracept, 1985, 1, pp 279–294.*
Collines, "Biochemical indices of potential fertility", Int J Gynecol Obstet, 1989, Supl. 1, pp 35–43.*
Collins et al., "Ovarian morphology, endocrine function and intra–follicular blood flow during the peri–ovulatory period", Human Reproduction, 1991, 6(3), pp 319–324.*
Collins (1991) Am J Obstet Gynecol, 165(6), p 1994–1996: 'The ecolution of reference methods to monitor ovulation'.
Collins (1992) Biochem Soc Trans, 20, p 234–237: 'Immunochemical tests of potential fertility'.
Colombo (1989) Int J Gynecol Obstet, Suppl 1, p 13–18: 'Biometrical research on some parameters of the menstrual cycle'.
Corsan et al Fertility and Sterility, (1990) 53(4), p 591–601: 'Home urinary luteinizing hormone immunoassays: clinical applications'.
Denari et al (1981) Obstetrics & Gynecology, 58 (1), p 5–9: 'Determination of Ovarian Function Using First Morning Urine Steriod Assays'.

Djerassi (1990) Science, June 1, 1990, p 1061–1062: 'Fertility Awareness: Jet–Age Rhythm Method?'.
Fabres et al (1993) Human Reproduction, 8 p 208–210: 'Validation of the dual analyte assay of the oestrone:pregnanediol ratio in monitoring ovarian function'.
Flynn (1989) Int J Gynecol Obstet, Suppl 1, p 123–127: 'Natural family planning and the new technologies'.
Fordney–Settlage (1981) Int J Fertil, 26, p 161–169: 'A Review of Cervical Mucus and Sperm Interactions in Humans'.
France et al (1975) J Reprod Fert, Suppl 22, p 107–120: 'The Detection of Ovulation in Humans and its Applications in Contraception'.
Garcia et al (1981) Fertility and Sterility, 36(3), p 308–315: 'Prediction of the Time of Ovulation'.
Gudgeon et al (1989) The Medical Journal of Australia, 152, p 344, 346 and 349: 'Evaluation of the accuracy of the home ovulation detection kit, Clearplan, at predicting ovulation'.
Hatcher et al (1994) Contraceptive Technology, 16th Revised Edn, Irvington Publishers, NY, p 327–340: 'Fertility Awareness'.
Ismail et al (1989) Contraception, 39(1), p 53–71: 'An evaluation of the Bioself 110 fertility indicator'.
Judge et al (19778) Steroids, 31(2), p 175–187: 'Time–Course Relationships between Serum LH, Serum Progesterone and Urinary Pregnanediol Concentrations in Normal Women'.
Katz et al (1991) Journal of Andrology, Jan./Feb. 1991, Abstract 29: 'Human Cervical Mucus Properties and Sperm Mucus Interection during the Proliferative Phase of the Menstrual Cycle'.
Katz (1991) Am J Obstet Gynecol, 165(6), Part 2, p 1984–1986: 'Human cervical mucus: Research update'.
Kerin et al (1981) British J Obstet Gynecol, 88(2), p. 81–90: 'Morphological and Functional Relations of Graafian Follicle Growth to Ovulation in Women Using Ultrasonic, Laparoscopic and Biochemical Measurements'.
Lauzon et al (1992) J. Steroid Biochem Molec Biol, 42(2), p 223–228: 'A Direct Dot–Enzyme Immunoassay to Detect Human Ovulation'.
Lewis et al (1993) New Zealand Medical Journal, Apr. 28, 1993, p 165–166: 'Recycling ovulation markers'.
Lewis et al (1994) Steroids, 59, p 288–291: 'Re–examining steroid hormone metabolites as ovulation markers using monoclonal antibodies'.
Landgren et al (1980) Acta Endocrinologia, 94, p 89–98: 'Hormonal profile of the cycle in 68 normally menstruating women'.
May (1989) Proceedings of "Biotec '89" Conference, Blenheim Online Publications, p 291–295: 'Clearblue One Step: adapting technology to the needs of the consumer'.
Moghissi et al (1972) Am J Obstet Gynecol, 114(3), p 405–418: 'A composite picture of the menstrual cycle'.
Moghissi (1980) Fertility and Sterility, 34(2), p 89–98 'Prediction and Detection of Ovulation'.
Moghissi (1992) Reproductive Endocrinology, 21(1), p 39–55: 'Ovulation Detection'.
Munro et al (1991) Clin Chem, 37 (6), p 838–844: 'Relationship of Serum Estradiol and Progesterone Concentrations to the Excretion Profiles of Their Major Urinary Metabolites as Measured by Enzyme Immunoassay and Radioimmunoassay'.

Paz et al (1990) *Gynecol Obstet Invest,* 29, p 207–210: 'Determination of Urinary Luteinizing Hormone for Prediction of Ovulation'.

*Population Reports,* Series 1, No. 3, Sep. 1991, p 1–33–1–71: 'Periodic Abstinence: How well do new approaches work?'.

Royston (1982) *Biometrics,* 38, p 397–406: 'Basal Body Temperature, Ovulation and the Risk of Conception, with Special Reference to the Lifetimes of Sperm and Egg'.

Royston (1991) *Statistics in Medicine,* 10, p 221–240: 'Identifying the Fertile Phase of the Human Menstrual Cycle'.

Schiphorst et al (1985) *Fertility and Sterility,* 44(3), p 328–334: 'An estrogen test to determine the times of potential fertility in women'.

Singh et al (1984) *Fertility and Sterility,* 41(2), p 210–217: 'Clinical validation of enzymeimmunoassay of human luteinizing hormone (hLH) in the detection of the preovulatory luteinizing (LH) surge in urine'.

Singh et al (1984) *Hormone Receptors in Growth andReproduction,* ed Saxena et al, Raven Press, NY, p 341–350: 'Clinical Validation of Enzyme Immunoassay for the Detection of the Preovulatory Luteinizing Hormone Surge in Urine'.

Stanczyk et al (1980) *Am J Obstet Gynecol,* 137(4), p 443–450: 'Direct radioimmunoassay of urinary estrogen and pregnanediol glucuronides during the menstrual cycle'.

*The Economist,* Mar. 23, 1991, p 128–129: 'Fertility: Keeping the beat'.

Tsibris et al (1989) *Int J Gynecol Obstet,* Suppl 1, p 73–82: 'Cervical mucus enzymes as markers of the woman's fertile period'.

Vermesh et al (1987) *Fertility and Sterility,* 47(2), p 259–264: 'Monitoring techniques to—predict and detect ovulation'.

Weerasekera et al (1983) *J Steroid Biochem,* 18(4), p 465–470: 'Multiple Immunoassay: The Simultaneous Measurement of Two Urinary Steroid Glucuronides as an Index of Ovarian Function'.

WHO Task Force (1980) *Am J Obstet Gynecol,* 138(4), p 383–390: 'Temporal relationships between ovulation and defined changes in the concentration of plasma estradiol–17 beta, luteinizing hormone, follicle–stimulating hormone, and progesterone'.

WHO Task Force (1981) *Am J Gynecol Obstet,* 139(8), p 886–895: 'Temporal relationships between ovulation and defined changes in the concentration of plasma estradiol–17beta, luteinizing hormone, follicle–stimulating hormone, and progesterone. II. Histologic dating'.

\* cited by examiner

MONITORING METHOD

This is a continuation of application Ser. No. 08/525,371, filed on Sep. 7, 1995, which was abandoned upon the filing hereof which was a Division of application Ser. No. 08/109, 503, filed Aug. 20, 1993, now U.S. Pat. No. 5,467,778 issued Nov. 21, 1995

This invention relates to methods, devices and test kits for use in monitoring the ovulation cycle in female mammals, especially humans.

The invention is particularly, although not solely, concerned with the provision of reliable information concerning fertility status as an aid to contraception, by the use of simple practical procedures that can readily be applied by unskilled persons, e.g. in the home.

Throughout this specification, the expression "fertile phase" is used to mean that interval in a female menstrual cycle, spanning the event of ovulation, during which it is most likely that intercourse will result in fertilization, because of the normal viability of spermatozoa and ova.

To provide reliable information concerning fertility status, the user must be given adequate warning of the onset of the fertile phase in the cycle. In general the proposed techniques rely on the monitoring of one or more parameters which alter as the event of ovulation approaches. Typical parameters which have been invoked are the concentration of a body fluid analyte, such as estradiol and metabolites thereof, for example estrone-3-glucuronide (E3G). Other parameters that have been used are basal body temperature and various physiological changes such as the characteristics of vaginal mucous.

Many excellent academic studies have been carried out using such parameters. Such studies have established how these parameters can be correlated with the fertility status of an average member of a large population sample.

However, when attempting to develop a practical monitoring system suitable for use by individuals, it is found that many individual subjects do not conform to the average in terms of cycle length and/or the duration and timing of the fertile phase. The extent of variation from one individual to another, and indeed, from one cycle to another in the same individual, renders average population data too unreliable for practical use.

A further factor that can vary widely from individual to individual is the threshold or baseline level of a parameter that is chosen as a testable characteristic which can signal the onset of the fertile phase. Again, although it may be possible to set an average threshold or baseline level from population data, this may be quite inappropriate for individual needs.

It is an objective of the present invention to establish a method of monitoring the ovulation cycle, useful for contraceptive purposes, which is tailored to the relevant characteristics of an individual subject by taking into account the foregoing possible variables.

Another important objective of the invention is to provide reliable fertility status while avoiding the necessity for tests to be conducted on a frequent (eg. daily) basis throughout every ovulation cycle. The necessity for regular, e.g. daily, testing throughout the cycle has characterised many ovulation cycle monitoring systems previously proposed.

There is a wealth of scientific literature on the urinary hormone profiles during the ovulation cycle. The relative usefulness of estradiol derivatives, especially estrone-3-glucuronide (E3G), lutenising hormone (LH), and progesterone derivatives, especially pregnanediol-3-glucuronide (P3G), as indicators of the status of the cycle, has been studied extensively.

Procedures are already available commercially to enable LH to be used to enhance the likelihood of conception.

The article "A prospective multicentre study to develop universal tests for predicting the female period in women" (WHO, *Int J Fertil* 30(3) 1985 p 18–30) discusses the prediction of the fertile phase in an ovulation cycle by measuring the daily levels of the hormones E3G and Pd-3-G (ie. P3G) in early morning urine. Although the primary purpose of this study is to analyse for differences in fertile phase calculation in different races of women, this paper does suggest that the relative levels of E3G and Pd-3-G may be used in predicting the start and end of the fertile phase. If the start of the fertile phase is defined by the sustained rise in the level of urinary E3G, then the end of that fertile phase (ie the start of the luteal phase) may be assumed to be 5 days after the E3G peak is observed. Similarly, if the start of the fertile phase is taken to be an increase in the E3G: Pd-3-G ratio, the end is defined as being 6 days after the peak value of this index is observed.

The article "New assays for identifying the fertile phase" by Brown, Blackwell, Holmes and Smyth (*Int J Gynecol Obstet* 1989 Suppl 1 p111–122) discusses the use of oestrogen level measurements as an ovulation predictor, although oestrogen on its own is stated as being an unreliable ovulation predictor. Pregnanediol is also suggested as a hormone marker to signify the end of the fertile phase. In the studies referred to in this paper, the average number of days of abstinence from intercourse per menstrual cycle was seventeen; furthermore, the user satisfaction with this method of contraception, and the willingness of test couples to continue using it, was found to be inversely related to length of the abstinence period. Daily hormone measurements were made, although the article does speculate that, when the fertile phase is predicted by E3G and P3G measurements, that 12 tests per month may be sufficient. In an effort to get the abstinence period down to the quoted "theoretical" minimum of seven days, it is suggested that it may be possible to use a method of fertile phase prediction using a combination of cervical mucus symptoms and non-symptomatic markers.

The article "Biochemical Indices of Potential Fertility" by Collins (*Int J Gynecol Obstet*, 1989, Suppl. 35–43) discusses the possible use of multiple analytes in urine to delineate the fertile phase. However, the tests carried out had a success rate in predicting the fertile phase of around 80% or less; also, the fertile phase predicted (and hence the abstinence period) was in all cases more than 10 days.

EP 367 615 (Monoclonal Antibodies Inc) provides a method of natural birth control in which the level of a urinary metabolite (progesterone) is measured as an indicator or the stage reached in the menstrual cycle. However, the only hormones suggested are progesterone metabolites, and hence the method can only be an indicator of the luteal phase safe period.

The article "Fertility Awareness: Jet-Age Rhythm Method?" by Djerassi (*Science*, Jun. 1, 1990, p 1061–2) suggests the prediction of the fertile phase for contraceptive, and in particular conception purposes by the analysis of body fluids (eg blood, urine or saliva). In this article, it is suggested that the start of the fertile phase could be predicted safely by detecting the rise in estradiol (or its metabolites). The start of the luteal phase could be predicted by either a second increase in estradiol concentration, or a major increase in progesterone (or its metabolites).

The clear inferences to be drawn from this literature are:
  estradiol and its metabolites, especially E3G, are the only
    urinary hormones that can be used to provide sufficiently early warning, during the pre-ovulation phase of the cycle, for contraceptive purposes; and any successful fertility awareness test which aims to provide adequate contraceptive information, must involve measurement of E3G or an equivalent molecule, and must identify the rise in E3G concentration that precedes ovulation.

Nevertheless, the literature (for example, Djerassi) also indicates that no satisfactory test based on E3G has yet been developed.

It is generally accepted that the background level of urinary E3G fluctuates so widely from individual to individual that no simple, universally applicable assay can be devised.

To try to overcome this problem, complicated mathematical procedures, eg. "CUSUM", have been evolved to calculate a threshold E3G concentration during a current ovulation cycle, and to identify any significant rise above the calculated threshold. Such systems have the disadvantage that by the time the mathematics has recognised that a significant rise is taking place, it may already be "too late" if the objective is contraception. Accordingly, it is generally accepted that the CUSUM approach cannot provide prospective information about fertility status. A review of CUSUM-based methods is found in Royston: *Statistics in Medicine*, Vol. 10 (1991) 221–240.

Overall, from this general survey of the prior art, it can be seen that in previously known techniques of fertile phase prediction, the period predicted is unduly long, giving rise to an unduly long period of abstinence. Very often, such as for example shown in EP 367 615, the long period of abstinence extends from menstruation to the end of the fertile phase. This, in part, is due to the difficulty in pinpointing the start of the fertile phase. It has also been a feature of prior art methods that frequent, often daily, measurements of urinary hormone levels throughout the current cycle have been necessary for the method to be deemed reliable as a method of contraception.

In the provision of reliable contraceptive advice, it is clearly very important that a monitoring method should give adequate warning of the onset of a fertile phase which happens to occur significantly in advance of normal. In this instance "normal" may be defined either in terms of population data, or normal for the individual subject herself.

The tendency has been to exercise extreme caution and to require testing of the relevant parameters throughout the cycle, and particularly right from the onset of the cycle (onset of menses). From the individual user's point of view, it is clearly advantageous if the necessity for such constant testing could be avoided and, instead, for the testing to be performed over a comparatively brief portion of each cycle. Not merely may this benefit the user in terms of convenience, but the cost of the method may also be reduced if, for example, fewer disposable testing devices are required each month.

In principle, based on population information, it should be possible to reduce the number of tests required by deciding that tests are unnecessary until a universally defined numerical day, or other specified time interval, following the onset of menses. However, as indicated above, individual variation tends to make any such universal assumption unsafe.

For the purposes of this specification, estradiol and all measurable estradiol metabolites, will collectively be referred to henceforth as "E3G". In addition to estrone-3-glucuronide already mentioned, estradiol metabolites that can also be assayed for the pruposes of the invention include estradiol-3-glucuronide, estriol-17-glucuronide, estriol-3-glucuronide, estriol-16-glucuronide and (principally for non-human subjects) estrone-3-sulphate. As will be appreciated from the following description, the invention can readily be applied to data derived from the measurement of body fluid concentrations of other analytes of significance in relation to the status of the ovulation cycle. Generally, the most suitable analytes are hormones and their metabolites. Follicle stimulating hormone (FSH) is an example. Examples of alternative body fluids, which are relatively accessible, are saliva, crevicular fluid, sweat, sebum, tears and vaginal fluid. In principle internal fluids, such as blood, can be used but are generally not preferred because they can only be accessed readily by invasive techniques.

The skilled reader will also appreciate that the body fluid "concentration" of the chosen analyte or analytes need not be measured in absolute terms, although this can of course be done if desired. Generally, it will be sufficient to assay an analyte in a manner which yields a signal, convertible to numerical data, related to the actual concentration, so that such data can be compared with similar data obtained at a different stage in the cycle to determine whether or not a significant change in actual concentration has occurred. Accordingly, where the specification and claims below refer to the "concentration" of an analyte, this expression should be interpreted broadly.

The invention provides a method of monitoring the status of a current ovulation cycle of an individual mammalian female subject, involving repeated testing of the body fluid concentration of at least one analyte of significance in relation to the status of the ovulation cycle during at least the pre-ovulation phase of the current ovulation cycle of the individual subject, wherein testing for said analyte concentration during the current ovulation cycle is commenced a plurality of days following the onset of menses but at least 2 numerical days in advance of the earliest numerical day on which actual ovulation has occurred in one or more previous ovulation cycles in the same individual subject; and an analyte concentration change indicative of imminent ovulation is identified from the results of such testing by reference to an analyte concentration reference value that has been adapted to the individual subject on the basis of analyte concentration test data obtained from the individual subject during one or more previous ovulation cycles.

The invention also provides a test kit comprising:
a) one or more testing devices for determining the concentration of said at least one analyte in said body fluid,
b) means enabling a user to derive from said concentration an indication of fertility status in the current ovulation cycle by reference to a concentration reference value determined from one or more previous ovulation cycles in the same subject; and
c) means enabling a user to derive a precise testing commencement day from knowledge of the numerical day on which actual ovulation occurred during at least one previous ovulation cycle in the same subject.

Conveniently, in such a test kit, wherein means b) and c) are combined, and ideally comprise electronic means programmed for use in a method according to the invention.

In a further embodiment, the invention provides an electronic means for use in a method of monitoring the status of a current mammalian ovulation cycle, programmed to process analyte concentration test data obtained from testing of a body fluid conducted during at least part of the pre-ovulation phase of the current cycle and to identify via said processing an analyte concentration change indicative of imminent ovulation, relative to an analyte concentration reference value that is adapted to an individual subject on the basis of analyte concentration test data obtained from the individual subject during one or more previous ovulation cycles, and also to identify an analyte testing commencement day falling a plurality of days following the onset of menses in the current ovulation cycle but at least 2 numerical day on which actual ovulation has occured in one or more previous ovulation cycles in the same individual subject.

Another aspect of the invention is a device for monitoring the human ovulation cycle, comprising means for initiating the recording of a cycle, means for measuring (if necessary in conjunction with one or more testing devices readable by the monitoring device) and recording urinary E3G concentration, means for determining a threshold urinary E3G concentration from measurements taken during the infertile and transition phases of at least one preceding cycle, and means for alerting a user if a measured urinary E3G concentration during the pre-fertile phase of a current cycle exceeds the determined threshold, means for measuring (if necessary in conjunction with one or more testing devices readable by the monitoring device) and recording urinary LH and/or P3G concentration, means for determining from such LH and/or P3G concentration the earliest numerical day on which actual ovulation occurred in one or more previous ovulation cycles, and means for alerting a user to an optimum E3G testing commencement day in the current cycle, said optimum E3G testing commencement day being at least 5 numerical days following the onset of menses in the current cycle but at least 2 numerical days in advance of said earliest numerical day on which actual ovulation occurred.

The analyte concentration may be measured in absolute terms, or in relative terms e.g. as a ratio relative to the concentration of a reference analyte present in the same sample of body fluid.

More generally, the invention includes any comparable method in which a body fluid characteristic (e.g. viscosity, ionic strength, or conductivity) of significance in relation to the status of the ovulation cycle, is compared to a reference value that is adapted to an individual subject on the basis of test data obtained from the individual subject during one or more previous ovulation cycles.

Optionally, the appropriate reference value, eg threshold, is derived from data obtained from a "rolling" reference base consisting of a fixed number of consecutive cycles immediately preceding the current cycle. Preferably this rolling reference base consists of the immediately preceding 4 to 10 cycles, more preferably the immediately preceding 5 or 6 cycles. By having such a rolling reference base, any progressive "drift" in the appropriate threshold in the individual concerned can be picked up. For example, the threshold for the next cycle can be an average of the thresholds suggested by the previous data, optionally weighted in favour of the most recent cycle or cycles.

Preferably, the method relies solely on the results of urine tests.

Preferably, the method does not involve the measurement of basal body temperature, especially as such measurement generally needs to be conducted throughout each cycle.

Preferably, the analyte is estradiol or a metabolite thereof, such as estrone-3-glucuronide.

A further embodiment of the invention is electronic means for use in a method of monitoring the status of a current mammalian, eg human, ovulation cycle, programmed to process analyte concentration test data obtained from testing of a body fluid conducted during at least part of the pre-ovulation phase of the current cycle, and to identify via said processing an analyte concentration change indicative of imminent ovulation, relative to an analyte concentration reference value that is adapted to an individual subject on the basis of analyte concentration test data obtained from the individual subject during one or more previous ovulation cycles.

Preferably, the electronic means is incorporated in a recording device having means to record the results of analyte concentration tests, and means to display information concerning the status of the current ovulation cycle of an individual subject whose analyte concentration has been tested. Preferably, the recording device has means to measure the result of an analyte concentration test conducted using a testing device presented to the recording device.

The invention includes a body fluid analyte concentration testing device when used in conjunction with an electronic means and recording device combination of the invention, which testing device comprises a body fluid sample collecting means and an immunochromatographic testing means which provides the test result in a form readable by the test result measuring means of the recording device.

Another aspect of the invention is a test kit for providing awareness of the status of a current mammalian, eg human, ovulation cycle, comprising one or more testing devices for determining the concentration (in relative or absolute terms) in a body fluid of an analyte of significance in relation to the status of the ovulation cycle, together with electronic means programmed to process analyte concentration test data obtained during at least part of the pre-ovulation phase of the current cycle and to identify therefrom an analyte concentration change indicative of imminent ovulation, relative to an analyte concentration reference value that is adapted to an individual subject on the basis of analyte concentration test data obtained from the individual subject during one or more previous ovulation cycles.

Preferably the test kit comprises a plurality of disposable body fluid testing devices.

In a particularly preferred test kit of the invention, wherein the principal analyte is estradiol or a metabolite thereof, such as E3G, usually measured in urine, the testing devices additionally test the urinary LH concentration of the individual subject, and the LH concentration test results so obtained are used by the electronic means in conjunction with the other analyte concentration test results.

An important aspect of the invention is a method of predicting the fertile phase during a current ovulation cycle of an individual mammalian, eg human, subject by detecting, in the pre-ovulation phase, a body fluid concentration change of an analyte of significance in relation to the status of the ovulation cycle, wherein the concentration change is determined by reference to a threshold concentration determined for the individual subject from measurements of the analyte concentration in the body fluid during the pre-ovulation phase of at least one previous ovulation cycle. Preferably the analyte is urinary E3G, in which event the urinary E3G threshold concentration adopted for the current cycle is preferably the concentration that is, in a previous ovulation cycle, exceeded more frequently during the total number of days constituting the transition phase of that previous cycle than during the same number of days in the infertile phase immediately preceding said transition phase.

The invention includes a device for monitoring the mammalian, eg human, ovulation cycle, comprising means for initiating the recording of a cycle, means for measuring (if necessary in conjunction with one or more testing devices readable by the monitoring device) and recording urinary E3G concentration, means for determining a threshold urinary E3G concentration from measurements taken during the infertile and transition phases of at least one preceding cycle, and means for alerting a user if a measured urinary E3G concentration during the pre-fertile phase of a current cycle exceeds the determined threshold. The invention also includes a kit for monitoring the mammalian, eg human, ovulation cycle, comprising such a device together with at least one testing device capable of being used to measure urinary E3G concentration.

A further aspect of the invention is an electronic means, such as a microprocessor, programmed for use in accordance with a method of the invention.

Nowhere in the literature is there any suggestion that the analyte concentration reference value, e.g. threshold level, should be calculated on the basis not of measurements taken during the current cycle, but instead from one or more previous cycles in the same individual.

The invention provides a composite method of monitoring the status of a current ovulation cycle and which method is closely tailored to the characteristics of the individual subject.

Preferably, testing is commenced at least 3, and more preferably at least 4, numerical days in advance of the earliest numerical day on which actual ovulation has occurred in one or more previous ovulation cycles in the same individual subject.

Preferably, the earliest actual ovulation day is derived from data collected during at least 3, and more preferably at least 5, consecutive previous cycles.

Ideally, the earliest ovulation day used to calculate the time interval for the purposes of the current cycle is derived from data obtained during at least the immediately preceding cycle.

A particularly convenient method involves the determination of the earliest previous ovulation day from data obtained from a "rolling" reference base consisting of a fixed number of consecutive cycles immediately preceding the current cycle. Preferably this rolling reference base consists of the immediately preceding 4 to 10 cycles, more preferably the immediately preceding 5 or 6 cycles. By having such a rolling reference base, any progressive "drift" in the occurrence of ovulation in the individual concerned can be picked up and accounted for in the allocation of the next testing commencement day.

The invention includes a test kit comprising one or more testing devices for determining the concentration (in relative or absolute terms) of said at least one analyte in said body fluid, together with instructions advising the user to commence said testing during said time interval, and means enabling a user to derive said time interval and/or a precise testing commencement day from knowledge of the numerical day on which actual ovulation occurred during at least one previous ovulation cycle.

More generally the invention can be applied in any method of monitoring the status of a current ovulation cycle of an individual mammalian, eg human, female subject involving the measurement of a parameter of significance in relation to the status of ovulation cycle and which exhibits a detectable change during the pre-ovulation phase of the cycle occurring at least 2 and more preferably at least 3 days in advance of the day of actual ovulation.

In a preferred embodiment of the invention, the choice of day for commencement of testing is influenced by the time interval between the onset of menses and the earliest numerical day on which actual ovulation has previously occurred. In some individuals there can be a comparatively long interval between the onset of menses and the first occurrence of ovulation. This is commonly observed in human individuals having cycle lengths which are frequently or always longer than the "28 day" population average. In such individuals there is a considerable risk that occasionally ovulation will occur exceptionally early (for that individual) and the testing commencement day should be brought forward to allow for this. Preferably the testing commencement day is calculated according to the following relationship:

| Earliest previous ovulation day | Testing commencement day |
|---|---|
| 8–10 | −4 |
| 11–14 | −5 |
| 15–18 | −6 |
| 19–23 | −7 |
| 24–28 | −8 |
| 29+ | −9 |

The parameter(s) chosen for providing the warning of imminent ovulation are not critical to the invention, provided that the parameter exhibits a detectable change within the time interval between the commencement of testing (as determined herein) and a safe time in advance of actual ovulation in the current cycle. In general, however, the most suitable parameter will be a change in the concentration (absolute or relative) of an analyte in a body fluid, especially a hormone or a metabolite thereof. The most appropriate body fluid is usually urine.

According to a preferred embodiment of the invention, for the purpose of determining the threshold applicable to an individual subject, it is convenient to sub-divide the portion of the ovulation cycle during which E3G level is relevant, into a number of distinct phases as follows:

i) The fertile phase, which can be regarded as the phase spanning days "−3" to "+2" inclusive relative to the day of actual ovulation. Ovulation day can be accurately pinpointed by measurement of urinary LH levels, for example, taking ovulation to occur on the day following LH maximum urinary concentration.

ii) The transition phase, during which warning of ovulation is required if the monitoring method is to provide a safe basis for contraceptive purposes. The transition phase can be regarded as the phase spanning days "−8" to "−4" inclusive relative to the day of actual ovulation.

iii) The infertile phase, which can be regarded as the phase from the onset of menses up to and including day "−9" relative to the day of actual ovulation.

The threshold level of urinary E3G should be determined from measurements of E3G concentration during the transition and pre-fertile phases of one or more previous cycles. While the threshold for the individual subject is being established, regular (preferably daily) measurements of urinary E3G concentration should be taken during these phases over at least one cycle and more preferably over at least two cycles, and ideally over at least three cycles. When more than one establishing cycle is used, these are preferably consecutive.

Actual ovulation can be determined, if desired, at the same time by methods already known per se, such as the detection of LH surge, P3G rise, or other bodily changes such as elevated basal body temperature (BBT). LH surge detection is most preferred for this purpose. The expression "LH surge" is used herein to mean the dramatic rise in LH concentration that precedes the event of ovulation. In the art, reference is made also to "LH max", i.e. the peak concentration of LH. In the majority of individuals, these are for all practical purposes simultaneous, when the cycle is monitored on a day-by-day basis. However, in a few individuals, perhaps 20% of the population, the actual peak concentration of LH is not observed until the day following the main concentration rise. For the purposes of the invention, we prefer to use the observable rise as the critical parameter.

After an appropriate E3G threshold has been established, regular E3G testing can be discontinued during the early part of the infertile phase of the current cycle. Instead, testing can be commenced at a set time after the onset of menses, for example.

If the method is to be used for contraceptive purposes, the user should be warned that the subject is at least likely to be fertile from the time an elevated level of E3G is detected.

For practical purposes, the threshold can be defined as the E3G concentration which is exceeded more frequently during the transition phase than during the infertile phase. For example, it may be exceeded on not more than 30% of the days in the infertile phase, but exceeded on not fewer than 60% of the days in the transition phase. More preferably the threshold is the E3G concentration which is exceeded on not more than 20% of the days in the infertile phase, but which is exceeded on not fewer than 80% of the days in the transition phase.

It will be found that the E3G threshold will vary widely from one individual subject to another, but generally will be in the range of about 5 to about 40 ng/ml. For many women, the threshold above which an elevated E3G level is recorded is about 30 ng/ml.

Although, if desired, a precise threshold could be derived for each individual subject, it is more convenient to simplify the method by using a range of "threshold bands" eg. 5, 10, 15, 20, 30, 40 and 50 ng/ml thresholds, and assigning a particular threshold band to each individual subject based on the E3G information derived in preceding cycles. We have found that the adoption of threshold bands is sufficiently accurate to enable reliable contraceptive advice to be obtained. The assays used in the method can be formulated to recognise when such bands have been exceeded.

In an article by Brown et al, *Int. J. Gynecol. Obstet.* 1989 Suppl. 1, pages 111–122, entitled "New assays for identifying the fertile period", a method is described in which urinary estrogen is measured, and the statement is made that:

" ... the daily increment in estradiol production during the rise to the pre-ovulatory peak is remarkably constant for all cycles, being very close to a factor of 1.4 per day."

As a population statistic, this quoted value of 1.4 for the daily increment during the pre-ovulatory rise may be correct, but in practice this factor varies very considerably from one individual to another. In an incremental or ratiometric method of deriving data from successive concentration assays of estradiol or a metabolite thereof (such as urinary E3G), it is unwise to rely on an increment of 1.4 as being a universal trigger significant of the pre-ovulatory rise. In practice we have found that the necessary trigger can be an incremental factor as high as 2.0, in which event a factor of 1.4 would not be significant in relation to the typical background fluctuations in E3G concentration in the individual concerned. In other individuals we have found that the necessary trigger is significantly lower than 1.4, and if a factor of 1.4 is chosen the pre-ovulatory E3G concentration rise would not be detected.

Accordingly, the present invention can be applied usefully in any method of monitoring the ovulation cycle which involves incremental ("ratiometric") analysis of a detectable variable parameter of significance during the pre-ovulatory phase of the cycle and wherein a warning of imminent ovulation is given when a pre-determined reference ratio is identified, the reference ratio having been determined for the individual subject based on data derived from one or more previous ovulation cycles in the same individual subject. The expression "analyte concentration reference value" as used herein includes reference values in ratio form.

The present invention can therefore be applied to advantage in any of the proposed assay systems which involve mathematical analysis of successive analyte concentrations, particularly urinary E3G concentrations by, for example, "CUSUM" analysis. Usually, the successive analyte concentrations (or indeed, successive measurements of any relevant parameter in accordance with the invention) are recorded on succcessive days.

Conveniently, the first assay of a current cycle is made at least 5 days after the commencement of menstruation.

Once an elevated E3G level, i.e. above a predetermined threshold, has been detected, although it cannot be said for certain that the woman has entered the fertile phase of her cycle, it can be said with reasonable certainly that the ovulation day of her cycle is imminent.

An advantage of the method is that it can work by single event trigger, e.g. the observation of an elevated level of one hormone, but one embodiment of the invention, 2 or more analytes are tested to provide comparative data, such as the concentration ratio of two analytes tested simultaneously.

The following description is provided in relation to the particular urinary hormones E3G, LH, and P3G, although it will be readily appreciated that the principles of the method can be used in relation to other biochemical markers, for example the hormones estradiol and progesterone, found for example in the blood or in saliva. The method of the invention may be applied to, or used in combination with observations of other physiological signs of the level of fertility in a female, of which she is aware, or can readily be made aware of, e.g. markers in other body fluids.

Where appropriate, exact ovulation date in the current cycle can be determined by any of the known chemical or physiological parameters, although a preferred method is by measuring the level of LH. Once the LH surge previously referred to has been detected, it can be said that ovulation of the user is imminent. Also, the day of the cycle on which ovulation has occurred can be noted for future reference. If the LH surge is detected, and hence the day of ovulation accurately pinpointed, it can be indicated to the user with a very high degree of certainty that the user will no longer be fertile four days hence (3 days after ovulation). For practical purposes, a urinary LH concentration of 20 mIU/ml can be regarded as a universal threshold indicative of the LH surge under virtually all circumstances.

A method for predicting the end of the fertile phase (though not so accurately the day of ovulation) is to measure the levels of the urinary hormone P3G. P3G has a relatively low level in urine until the start of the luteal phase, at which point its level rises fairly sharply. Therefore, once an elevated level of P3G is detected, it can be indicated to the user that the luteal phase of the cycle—ie. the terminal infertile period—has commenced. An elevated level of urinary P3G can be based on data taken during the current and/or one or more preceding cycles. An "elevated" P3G level can be recorded, for example, when either the level of P3G detected is greater than the sum of the four previous recorded levels of P3G in the same menstrual cycle, or greater than 3500 ng/ml, whichever of these two thresholds is lower and is first achieved. Once an "elevated" P3G level is recorded, the user can be that she is infertile for the remainder of that cycle.

In a preferred embodiment, the detection of either LH or P3G can be used as a trigger to indicate to the user that the user is no longer fertile until the end of the cycle, with one hormone acting as a "back up" to the other. However, it is preferred that the detection of LH be used as a primary indicator of whether ovulation has or is about to occur, since the detection of LH lends itself to more accurate determination of the exact ovulation day than the use of P3G.

The method of the invention has the advantage that it allows, with a high degree of accuracy, the determination of an ovulation day, and hence a fertile phase, within a cycle. When needed for contraception purposes, this leads to a method of prediction of the fertile phase which requires a minimal period of abstinence from unprotected intercourse within any given menstrual cycle.

The method also has the advantage in that it may require less testing within a given month, and hence reduced expense and inconvenience to the user, without any prejudice to the reliability. Detection of an LH peak is not essential, although the detection of the LH peak can be used as a "back up" warning of possible fertility in the event that no elevated E3G level is observed.

The method of the invention also has the advantage in that it is independent of the need to input body basal temperature data, hence avoiding a time consuming, inconvenient and arguable unreliable procedure for the user to carry out.

The invention also provides a device for monitoring the ovulation cycle of a female mammal comprising means for initiating the recording of a cycle, means for measuring (if necessary in conjunction with one or more testing devices readable by the monitoring device) and recording urinary E3G concentration, means for determining a threshold E3G concentration from measurements taken during the infertile and transition phases of at least one preceding cycle, and means for alerting a user if a measured E3G concentration during the transition phase of a current cycle exceeds the determined threshold.

The initiating means can for example, be an input means such as a switch or button which the user can actuate at the commencement or termination of menses.

Preferably, the monitoring device of the invention also incorporates means for determining actual ovulation, for example by incorporating means to measure and record LH surge or a rise in urinary P3G concentration.

Information can be conveyed to the user by means of a liquid crystal or LED display, for example. If desired, information on the state of fertility can be conveyed by a simple visual indication, eg a combination of colours showing, for example, green for infertile, red for fertile, and yellow for any intermediate stage when conception is less likely but still possible. Conveniently, the red and yellow signals on the device may be combined, such that the device indicates "red" signal to the user whenever conception is possible. Especially if the device is intended primarily as an aid to contraception, it should "fail safe" by showing a "fertile" signal.

The monitoring device should be programmed to modify (if necessary) its prediction of appropriate threshold for the present cycle, or for a future cycle, on the basis of actual measurements recorded during one or more previous cycles.

The invention further provides a kit for monitoring the ovulation cycle of a female mammal, comprising a monitoring device as set forth above, together with at least one testing device capable of being used to measure the level of one or more urine components. It is envisaged that the monitoring device will generally be of a relatively durable nature and capable of being used over a considerable number of cycles. The testing devices for measuring the urine components are preferably disposable after individual use, and it is therefore envisaged that the user of the monitoring device will need to replenish the testing devices.

An embodiment of the invention is a plurality of disposable body fluid (eg urine) testing devices, packaged with instruction for use in a method according to the invention. These testing devices, where appropriate, can be urine testing devices from each of which the urinary concentrations of E3G and LH (and/or P3G) can be determined (where necessary, in conjunction with a monitor device or electronic means as set forth herein).

Methods of detecting body fluid analytes, such as urinary hormone metabolites, suitable for the purposes of this method, are well known to those skilled in the art. In a preferred embodiment, the analyte is detected by assay methods and devices as described in our UK patent GB 2204398, the contents of which are incorporated herein by reference.

Where the method of the invention relies on measurement of a urine component, this must be done on a urine sample. A variety of immunoassay techniques are available which enable urine components to be measured. A wide variety of solid phase testing devices such as dipsticks and chromatographic strips have been described in the literature, and can readily be adapted for use in determining urinary analytes. The device should at least be capable of indicating relative levels of analyte, eg. E3G, in threshold bands. Examples of simple assay technology that can readily be adapted for use in the home is described, for example, in EP 0225054, EP 0183442, EP 0186799, GB 2204398 and EP383619 the disclosures of these publications being incorporated herein by conference. Disposable assay strips such as those described in GB 2204398 and EP 383619 which simply require to be contacted with urine and which provide an assay result in semi-qualitative form, eg. by means of a series of test zones on the strip which are progressively positive at higher urinary analyte levels, can be used. Multiple strips that respond at different analyte thresholds can be used, rather than a single strip. Alternatively, a visually readable quantitative assay can be based on progression of a visible, eg. coloured, region or "front" over a surface (eg. radial diffusion), using for example an enzyme-labelled assay.

In a more sophisticated version of an apparatus according to the invention, the recording device can incorporate means for reading the result of the urine assay, eg. by measuring the reflectance or fluorescence from an assay strip. This may enable a more precise numerical indication to be given of the analyte level, and further enhance the accuracy of the method.

In an embodiment of the invention in which two or more analytes are measured simultaneously, such measurement can if desired be performed using a single body fluid testing device, eg. a device incorporating multiple assay strips, or a single strip capable of independently detecting the level of the different analytes.

The detailed electronics of a recording device capable of assimilating, remembering and handling analyte concentration data, as well as providing the preferred electronic features of the device discussed herein, and predicting future cycles on the basis of such data, can readily be provided by those skilled in the electronics art once they have been advised of the factors that such a device must take into consideration, and the information that the device must provide for the user. Such detailed electronics do not form part of the invention. However, by way of example only, the basic functions that may be required in such a device are outlined in FIG. 3 of the accompanying drawings and described briefly below.

If the device for measuring the levels of hormones in the test sample is electronic, conveniently it contains a facility which automatically varies the threshold level of E3G for a particular user, for example from 30 ng/ml to 20 ng/ml or 40 ng/ml if the observed abstinence period for a particular user is undesirably long or short.

By way of example only, practical aspects of the invention are described below with reference to the accompanying drawings, of which.

Figure 1:
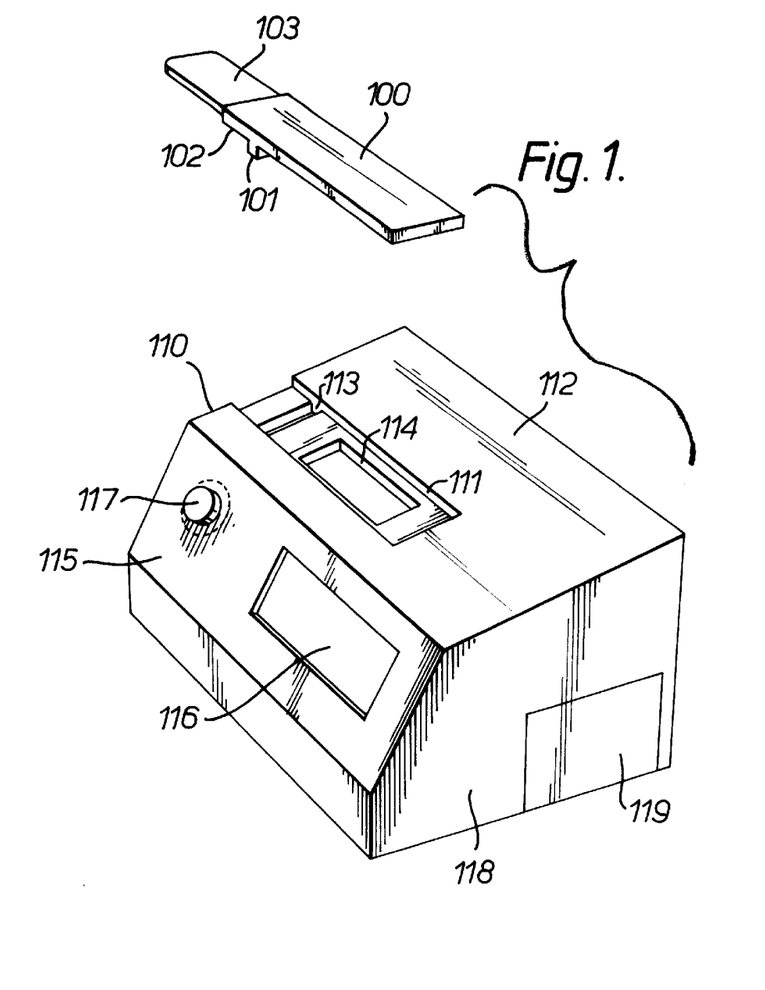
FIG. 1 of the accompanying drawings illustrates an ovulation cycle monitoring device for use in accordance with the invention, together with an associated urine sample testing device.

Referring to FIG. 1, the urine sample testing device comprises a flat elongate casing 100 having a locating ridge 101 on its lower surface 102. Projecting from one end of the casing is a bibulous sample receiving member 103.

The monitor comprises a casing 110 having a recess 111 in its upper surface 112 to accommodate the casing 100 of the testing device. Recess 111 incorporates a locating slot 113 into which the locating ridge 101 on the casing of the testing device can be inserted to positively locate the testing device in relation to a reading window 114 in the recess. Casing 110 contains means (not shown) such as a fluorescence reader to measure the result of a urinary analyte concentration assay performed using the testing device.

The sloping front face 115 of the monitor casing incorporates a large window 116 through which information can be conveyed to the user eg. by means of an LED display or other visual output. This information can be provided in a variety of forms, such as an indication of a calender and the need to perform urine tests, and an indication of the current status of the ovulation cycle. The sloping face 115 of the casing also incorporates a button 117 which the user can press to indicate the commencement of an ovulation cycle and to start the monitor processing information relative to that cycle.

In general the monitor will be battery-powered, and incorporates in side 118 of the casing an access point such as a removable cover 119 to permit batteries to be inserted and changed.

Figure 2:
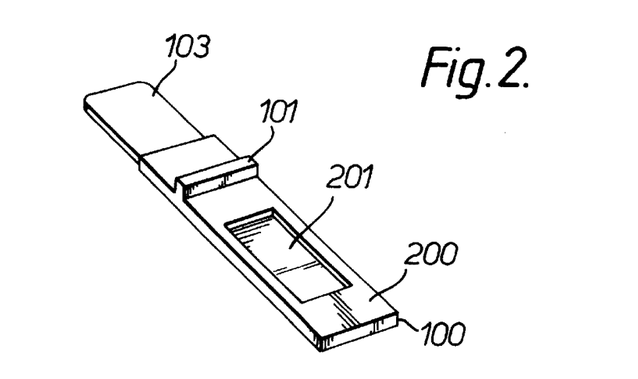
FIG. 2 shows the urine testing device in greater detail.

Referring to FIG. 2, the testing device is shown inverted relative to the aspect seen in FIG. 1. The locating ridge 101 is now on the upper surface 200. Also in the surface 200 now uppermost is a result window 201. The body of the testing device can incorporate an immunochromatograhic strip (not shown) incorporating all necessary reagents to enable an immunoassay to be formed which detects the presence and concentration of analyte in a urine sample applied to the sample collecting member 103. The result of the assay can be effected by the immobilization of a labelled component, via a sandwich or competition reaction in the presence of analyte in an applied urine sample, the labelled reagent becoming concentrated in a zone revealed through the result window. When the testing device is inverted and located in the recess 111 in the casing of the monitor, the result window is immediately adjacent to the reading window 114 in the monitor and the assay result can be determined. For example, if the label is a fluorescent reagent, the reading means within the monitor can detect and measure fluorescent light output from the accumulated label in the detection zone on the strip to provide a numerically accurate concentration value for the analyte in the urine sample. This information can be processed by the monitor together with calender information resulting from the initiation of the cycle process by the user and historical data which the monitor can retain from previous cycles.

Figure 3:
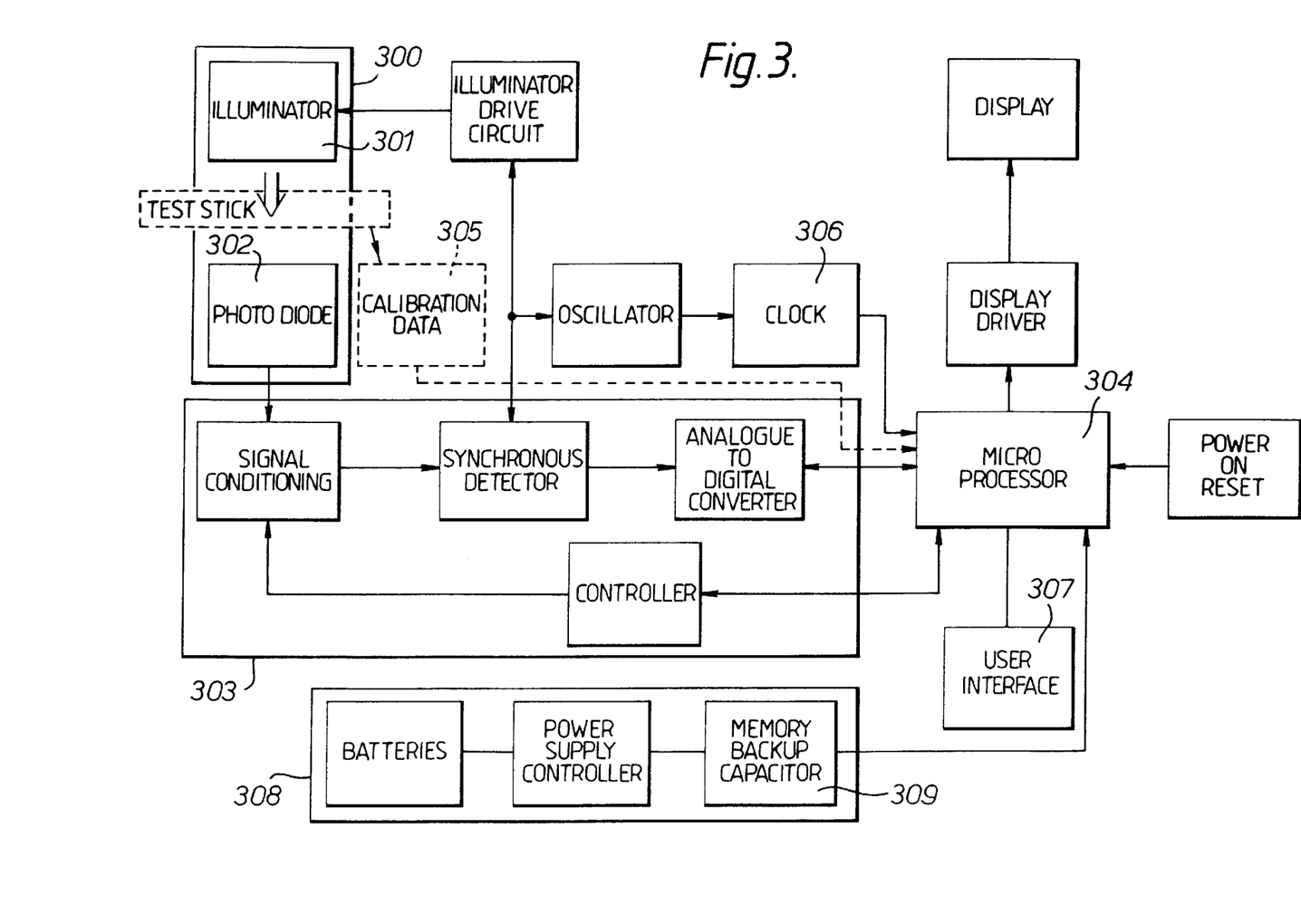
FIG. 3 shows, in schematic form, the basic functions that may be required in an electronic monitor for use in accordance with the invention.

Referring to FIG. 3, some of the basic elements which may be required in an electronic monitoring device are seen. The individual features can be entirely conventional, and those familiar with the art of electronics will appreciate that other combinations and arrangements of such features can be employed to achieve the objectives of the invention. For example, so-called "hard-wired" systems, and "neural networks", can be used in place of conventional microprocessors based on "chip"technology. As depicted in FIG. 3, the combination essentially comprises:

A reading unit 300 to derive information from a test device, such as a test stick, the reading unit comprising an illuminator 301 and a reader 302 (represented here as a photo diode). The reading unit feeds into a conversion unit 303 to convert the optical signal into a form usable by a microprocessor 304. As an optional feature, a calibration system 305 is provided to convert the signal derived from the reading unit into data corresponding, for example, to an absolute concentration value. A timer, such as a clock 306 is required to regulate measurements within a cycle. The microprocessor 304 processes, memorizes and interprets results in the light of previous events, particularly recorded from previous cycles. The user interface 307 will generally comprise at least means, such as a push button, which the user can operate at the commencement of a cycle to initiate the operation of the device as a whole. The power supply 308 should include means, such as a memory back up capacitator 309, to prevent loss of historical data if it becomes necessary to replace batteries.

Aspects of the invention are illustrated in the following Examples. These relate to the monitoring of the human ovulation cycle.

The example shows E3G profiles from two women—one known to have low levels of urinary E3G and the other known to have relatively high levels. In the first two columns of each table, 30 days of each cycle are set out in terms of their fertility. The first phase is termed infertile and consists of that portion of the follicular phase during which unprotected intercourse would not be expected to result in conception. This is followed by the transition phase, during which changes occur that lead to a fertile state. It is within this phase that the system must receive a positive signal to indicate the onset of the fertile phase. The fertile phase is that phase before and after ovulation during which unprotected intercourse is most likely to result in conception. Its duration before ovulation is dictated entirely by the effective lifetime of sperm, and this, in turn is influenced by factors controlled by the female hormones, especially mucus. The post fertile, luteal phase is that time after which the ovum has left the uterus and conception in the current cycle is no longer possible.

E3G values for the first 20 days of each cycle are given in the third column. These were derived by immunoassay on early morning urine samples collected each day. The immunoassay was a conventional enzyme-labelled-antigen competitive assay. The values given are in ng/ml.

Actual ovulation is taken as 24 hours following the LH maximum value. These LH values were determined by conventional immunoassay on the same samples, but the values are not included in the table as ovulation date is the essential result.

The following "rules" were employed in determining an appropriate threshold for the next cycle:
1. E3G thresholds can be values of 5, 10, 15, 20, 25 and 30 ng/ml, but not higher.
2. The ideal length of warning is 6 days before ovulation.
3. Threshold exceedance on the 4th and 5th days of the Transition Phase is more important than on the earlier days of the Transition Phase.
4. The first chosen threshold should be the lowest value exceeded most frequently during the Transition Phase, and least frequently in the Infertile Phase of the "learning" cycle. Preferably, it should not be exceeded at any time during the Infertile Phase.
5. For the first cycle, testing should be done each day, until the LH surge is identified, since this is the major "learning" phase.
6. In subsequent cycles, the threshold can be modified if
   a) the chosen threshold is not exceeded on days 4 and/or 5 of the Transition Phase;
   b) the chosen threshold is unnecessarily lower than needed to trigger on days 4 and/or 5 of the Transition Phase.
7. E3G levels in the first 5 days of each cycle were ignored, on the assumption that in a home-use test, sampling would not be commenced immediately following menses.

Following the initial cycle in each individual, a testing commencement day (identified by "****") applicable in a home-use situation was chosen for the next cycle in accordance with the tabulated relationship given earlier in this specification. Thus, for example, following cycle A1 in which actual ovulation occurred on numerical day 18, the chosen testing commencement day for cycle A2 was numerical day 12 (18-6).

Examining cycle A2 it can be seen that, in practice, commencing testing on day 12 would have coincided with the beginning of the E3G rise indicative of imminent ovulation. Actual ovulation occurred on day 17. Applying the tabulated relationship the testing commencement day chosen for cycle A3 was numerical day 11.

In practice in cycle A3 numerical day 11 was merely 4 days in advance of actual ovulation which occurred on day 15. The testing commencement day chosen for cycle A4 was day 9.

It can be seen from cycle A4 that day 9 was 5 days in advance of actual ovulation (on day 14) and that the recommended testing commencement day for the following cycle was also day 9.

In cycle A5, actual ovulation occurred on day 17 and probably the drift of actual ovulation towards earlier days in successive cycles in this individual had ceased, and actual ovulation is reverting to a more "normal" timing. The recommended testing commencement day should however remain as numerical day 9, at least for the time being, to cope with another early drift of ovulation day.

This series of cycles shows the advantage of using a succession of consecutive cycles to establish the optimum testing commencement day.

For individual B the testing commencement day recommended from cycle B1 was numerical day 13, which was modified after cycle B2 to numerical day 11, and after cycle B4 to day 10.

With regard to the appropriate EJG threshold, in cycle 1 of individual B, the value of 25 is exceeded on days 8 and 11, (in the infertile phase) so the threshold should, preferably, be above this value. 30 is exceeded on the 4th and 5th days of the transition (days 15 and 16), so 30 is chosen, as that is the highest threshold option available, and it conforms to rules 2, 3 and 4.

In cycle 3, the 30 threshold worked, but on day 13 (the 5th transition day) the value was 23.9 so, according to rule 6a, the threshold should be lowered to 20, being the highest option exceeded on that day.

In cycle 4, according to rule 6b, a new threshold of 25 should be adopted, because the two available transition days show that 20 is unnecessarily low and that 25 works just as well.

In cycle 5, following rules 2, 3 and 6b, a revised threshold of 30 is adopted for the next cycle.

The first day on which the chosen E3G threshold is exceeded is highlighted (****).

INDIVIDUAL A
CYCLE A 1: Profile-establishing cycle

| Day | Phase | E3G value | Actual Ovulation |
|---|---|---|---|
| 1 | infertile | 2.7 | |
| 2 | " | 3.3 | |
| 3 | " | 2.4 | |
| 4 | " | 1.8 | |
| 5 | " | 3.6 | |
| 6 | " | 2.5 | |
| 7 | " | 1.7 | |
| 8 | " | 1.9 | |
| 9 | " | 3.1 | |
| 10 | transition | 5.4 | |
| 11 | " | 2.1 | |
| 12 | " | 5.3 | |
| 13 | " | 10.5 | |
| 14 | " | 7.7 | |
| 15 | fertile | 5.2 | |
| 16 | " | 8.3 | |
| 17 | " | 6.8 | |
| 18 | " | 4.3 | LHM + 1 |
| 19 | " | 4.9 | |
| 20 | " | 5.3 | |
| 21 | postfertile | | |
| 22 | " | | |
| 23 | " | | |
| 24 | " | | |
| 25 | " | | |
| 26 | " | | |
| 27 | " | | |
| 28 | " | | |
| 29 | " | | |
| 30 | " | | |

Days warning of ovulation: none this month (establishing parameters)

Chosen E3G Threshold for next cycle: 5 ng/ml

Chosen testing commencement day for next cycle: 12

CYCLE A 2

| Day | Phase | E3G value | Actual Ovulation |
|---|---|---|---|
| 1 | infertile | 2.0 | |
| 2 | " | 1.5 | |
| 3 | " | 1.1 | |
| 4 | " | 4.1 | |
| 5 | " | 4.0 | |
| 6 | " | 3.5 | |
| 7 | " | 2.3 | |
| 8 | " | 1.9 | |

CYCLE A 2 -continued

| Day | Phase | E3G value | Actual Ovulation |
|---|---|---|---|
| 9 | transition | 3.6 | |
| 10 | " | 3.7 | |
| 11 | " | 3.0 | |
| 12*** | " | 9.2**** | |
| 13 | " | 8.9 | |
| 14 | fertile | 14.6 | |
| 15 | " | 12.6 | |
| 16 | " | 8.8 | |
| 17 | " | 15.8 | LHM + 1 |
| 18 | " | 6.9 | |
| 19 | " | 6.5 | |
| 20 | postfertile | 6.5 | |
| 21 | " | | |
| 22 | " | | |
| 23 | " | | |
| 24 | " | | |
| 25 | " | | |
| 26 | " | | |
| 27 | " | | |
| 28 | " | | |
| 29 | " | | |
| 30 | " | | |

Days warning of ovulation: 6 days

Chosen E3G Threshold for next cycle: 5 ng/ml
Chosen testing commencement day for next cycle: 11

CYCLE A 3

| Day | Phase | E3G value | Actual Ovulation |
|---|---|---|---|
| 1 | infertile | 2.0 | |
| 2 | " | 2.0 | |
| 3 | " | 2.7 | |
| 4 | " | 2.9 | |
| 5 | " | 2.7 | |
| 6 | " | 1.6 | |
| 7 | transition | 2.5 | |
| 8 | " | 5.4 | |
| 9 | " | 4.0 | |
| 10 | " | 5.6 | |
| 11*** | " | 3.7 | |
| 12 | fertile | 6.2**** | |
| 13 | " | 23.6 | |
| 14 | " | 21.3 | |
| 15 | " | 8.3 | LHM + 1 |
| 16 | " | 4.5 | |
| 17 | " | 3.7 | |
| 18 | postfertile | 3.4 | |
| 19 | " | 2.8 | |
| 20 | " | 3.1 | |
| 21 | " | | |
| 22 | " | | |
| 23 | " | | |
| 24 | " | | |
| 25 | " | | |
| 26 | " | | |
| 27 | " | | |
| 28 | " | | |
| 29 | " | | |
| 30 | " | | |

Days warning of ovulation: 3 days
Chosen E3G Threshold for next cycle: 5 ng/ml
Chosen testing commencement day for next cycle: 9

CYCLE A 4

| Day | Phase | E3G value | Actual Ovulation |
|---|---|---|---|
| 1 | infertile | 2.4 | |
| 2 | " | 2.8 | |
| 3 | " | 5.2 | |
| 4 | " | 3.6 | |
| 5 | " | 2.5 | |
| 6 | transition | 3.1 | |
| 7 | " | 3.9 | |
| 8 | " | 4.6 | |
| 9*** | " | 5.1**** | |
| 10 | " | 6.1 | |
| 11 | fertile | 16.7 | |
| 12 | " | 10.8 | |
| 13 | " | 22.8 | |
| 14 | " | 21.3 | LHM + 1 |
| 15 | " | 9.4 | |
| 16 | " | 12.2 | |
| 17 | postfertile | 5.7 | |
| 18 | " | 5.2 | |
| 19 | " | 7.5 | |
| 20 | " | 9.0 | |
| 21 | " | | |
| 22 | " | | |
| 23 | " | | |
| 24 | " | | |
| 25 | " | | |
| 26 | " | | |
| 27 | " | | |
| 28 | " | | |
| 29 | " | | |
| 30 | " | | |

Days warning of ovulation: 6 days
Chosen E3G Threshold for next cycle: 5 ng/ml
Chosen testing commencement day for next cycle: 9

CYCLE A 5

| Day | Phase | E3G value | Actual Ovulation |
|---|---|---|---|
| 1 | infertile | 2.3 | |
| 2 | " | 2.8 | |
| 3 | " | 2.7 | |
| 4 | " | 2.3 | |
| 5 | " | 2.8 | |
| 6 | " | 4.8 | |
| 7 | " | 5.6 | |
| 8 | " | 4.5 | |
| 9*** | transition | 3.2 | |
| 10 | " | 8.5**** | |
| 11 | " | 7.3 | |
| 12 | " | 6.3 | |
| 13 | " | 7.0 | |
| 14 | fertile | 11.8 | |
| 15 | " | 19.3 | |
| 16 | " | 18.5 | |
| 17 | " | 9.2 | LHM + 1 |
| 18 | " | 5.3 | |
| 19 | " | 4.8 | |
| 20 | postfertile | 6.1 | |
| 21 | " | | |
| 22 | " | | |
| 23 | " | | |
| 24 | " | | |
| 25 | " | | |

CYCLE A 5 -continued

| Day | Phase | E3G value | Actual Ovulation |
|---|---|---|---|
| 26 | " | | |
| 27 | " | | |
| 28 | " | | |
| 29 | " | | |
| 30 | " | | |

Days warning of ovulation: 7 days

Chosen E3G Threshold for next cycle: 5 ng/ml
  Chosen testing commencement day for next cycle: 9

INDIVIDUAL B
CYCLE B 1: Profile-establishing cycle

| Day | Phase | E3G value | Actual Ovulation |
|---|---|---|---|
| 1 | infertile | 10.9 | |
| 2 | " | 15.2 | |
| 3 | " | 21.2 | |
| 4 | " | 12.7 | |
| 5 | " | 11.8 | |
| 6 | " | 16.5 | |
| 7 | " | 15.6 | |
| 8 | " | 25.1 | |
| 9 | " | 10.1 | |
| 10 | " | 16.8 | |
| 11 | " | 28.2 | |
| 12 | transition | 24.6 | |
| 13 | " | 28.7 | |
| 14 | " | 27.7 | |
| 15 | " | 62.6 | |
| 16 | " | 68.5 | |
| 17 | fertile | 61.9 | |
| 18 | " | 103.4 | |
| 19 | " | 85.4 | |
| 20 | " | 45.4 | LHM + 1 |
| 21 | " | | |
| 22 | " | | |
| 23 | postfertile | | |
| 24 | " | | |
| 25 | " | | |
| 26 | " | | |
| 27 | " | | |
| 28 | " | | |
| 29 | " | | |
| 30 | " | | |

Days warning of ovulation: none this month (establishing parameters)

Chosen E3G Threshold for next cycle: 30 ng/ml
  Chosen testing commencement day for next cycle: 13

CYCLE B 2

| Day | Phase | E3G value | Actual Ovulation |
|---|---|---|---|
| 1 | infertile | 27.5 | |
| 2 | " | 28.8 | |
| 3 | " | 24.7 | |
| 4 | " | 22.6 | |
| 5 | " | 24.9 | |
| 6 | " | 28.9 | |
| 7 | " | 14.6 | |

CYCLE B 2 -continued

| Day | Phase | E3G value | Actual Ovulation |
|---|---|---|---|
| 8 | " | 8.4 | |
| 9 | " | 24.7 | |
| 10 | transition | 33.6 | |
| 11 | " | 39.3 | |
| 12 | " | 25.6 | |
| 13*** | " | 43.2**** | |
| 14 | " | 67.1 | |
| 15 | fertile | 62.0 | |
| 16 | " | 94.6 | |
| 17 | " | 58.4 | LHM + 1 |
| 18 | " | 42.4 | |
| 19 | " | 60.4 | |
| 20 | " | 56.0 | |
| 21 | postfertile | | |
| 22 | " | | |
| 23 | " | | |
| 24 | " | | |
| 25 | " | | |
| 26 | " | | |
| 27 | " | | |
| 28 | " | | |
| 29 | " | | |
| 30 | " | | |

Days warning of ovulation: 4 days

Chosen E3G Threshold for next cycle: 30 ng/ml
  Chosen testing commencement day for next cycle: 11

CYCLE B 3

| Day | Phase | E3G value | Actual Ovulation |
|---|---|---|---|
| 1 | infertile | 46.4 | |
| 2 | " | 30.0 | |
| 3 | " | 12.4 | |
| 4 | " | 6.5 | |
| 5 | " | 8.7 | |
| 6 | " | 17.2 | |
| 7 | " | 14.9 | |
| 8 | " | 11.8 | |
| 9 | transition | 11.0 | |
| 10 | " | 13.1 | |
| 11*** | " | 25.6 | |
| 12 | " | 32.5**** | |
| 13 | " | 23.9 | |
| 14 | fertile | 63.8 | |
| 15 | " | 22.1 | |
| 16 | " | 65.9 | |
| 17 | " | 41.2 | LHM + 1 |
| 18 | " | 7.6 | |
| 19 | " | 35.3 | |
| 20 | postfertile | 33.7 | |
| 21 | " | | |
| 22 | " | | |
| 23 | " | | |
| 24 | " | | |
| 25 | " | | |
| 26 | " | | |
| 27 | " | | |
| 28 | " | | |
| 29 | " | | |
| 30 | " | | |

Days warning of ovulation: 6 days
Chosen E3G Threshold for next cycle: 20 ng/ml
Chosen testing commencement day for next cycle: 11 (no change)

CYCLE B 4

| Day | Phase | E3G value | Actual Ovulation |
|---|---|---|---|
| 1 | infertile | 17.7 | |
| 2 | " | 12.2 | |
| 3 | " | 7.2 | |
| 4 | " | 6.2 | |
| 5 | " | 13.9 | |
| 6 | " | 12.9 | |
| 7 | " | 12.7 | |
| 8 | transition | 9.3 | |
| 9 | " | 16.5 | |
| 10 | " | 17.7 | |
| 11*** | " | 26.0**** | |
| 12 | " | 38.3 | |
| 13 | fertile | 70.6 | |
| 14 | " | 74.6 | |
| 15 | " | 70.6 | |
| 16 | " | 49.7 | LHM + 1 |
| 17 | " | 23.5 | |
| 18 | " | 29.8 | |
| 19 | postfertile | 44.4 | |
| 20 | " | 32.7 | |
| 21 | " | | |
| 22 | " | | |
| 23 | " | | |
| 24 | " | | |
| 25 | " | | |
| 26 | " | | |
| 27 | " | | |
| 28 | " | | |
| 29 | " | | |
| 30 | " | | |

Days warning of ovulation: 6 days
Chosen E3G Threshold for next cycle: 25 ng/ml
Chosen testing commencement day for next cycle: 10

CYCLE B 5

| Day | Phase | E3G value | Actual Ovulation |
|---|---|---|---|
| 1 | infertile | 33.9 | |
| 2 | " | 27.3 | |
| 3 | " | 20.2 | |
| 4 | " | 7.0 | |
| 5 | " | 12.7 | |
| 6 | " | 7.2 | |
| 7 | " | 14.5 | |
| 8 | " | 14.8 | |
| 9 | " | 10.8 | |
| 10*** | transition | 8.7 | |
| 11 | " | 14.1 | |
| 12 | " | 17.4 | |
| 13 | " | 41.3**** | |
| 14 | " | 57.5 | |
| 15 | fertile | 42.0 | |
| 16 | " | 55.4 | |
| 17 | " | 60.1 | |
| 18 | " | 39.4 | LHM + 1 |
| 19 | " | 24.7 | |
| 20 | " | 10.5 | |
| 21 | postfertile | | |
| 22 | " | | |
| 23 | " | | |
| 24 | " | | |
| 25 | " | | |
| 26 | " | | |
| 27 | " | | |
| 28 | " | | |
| 29 | " | | |
| 30 | " | | |

Days warning of ovulation: 6 days
Chosen e3g threshold for next cycle: 30 ng/ml
Chosen testing commencement day for next cycle: 10 (no change)

What is claimed is:

1. A test kit for conducting a method of monitoring the status of a current ovulation cycle of an individual mammalian female subject, involving repeated testing of the body fluid concentration of at least one analyte of significance in relation to the status of the ovulation cycle during at least the pre-ovulation phase of the current ovulation cycle of the individual subject, comprising:

a) one or more testing devices for determining the concentration of said at least one analyte in said body fluid, b) means enabling a user to derive from said concentration an indication of fertility status in the current ovulation cycle by reference to a concentration reference value determined from one or more previous ovulation cycles in the same subject; and c) means for determining the day on which actual ovulation occurred during at least one previous ovulation cycle; and d) means enabling a user to derive a precise testing commencement day from knowledge of the numerical day on which actual ovulation occurred during at least one previous ovulation cycle in the same subject.

2. A test kit according to claim 1, wherein means b) and c) are combined.

3. A test kit according to claim 1, wherein means b) and c) comprise electronic means.

4. A test kit according to claim 1, incorporating a plurality of disposable body fluid testing devices.

5. A plurality of disposable body fluid testing devices, packaged with instructions for use in a method according to claim 1.

6. A device for monitoring the human ovulation cycle, comprising means for initiating the recording of a cycle, means for measuring and recording urinary E3G concentration, means for determining a threshold urinary E3G concentration from measurements taken during the infertile and transition phases of at least one preceding cycle, and means for alerting a user if a measured urinary E3G concentration during the pre-fertile phase of a current cycle exceeds the determined threshold, means for measuring and recording urinary LH and/or P3G concentration, means for determining from such LH and/or P3G concentration the earliest numerical day on which actual ovulation occurred in one or more previous ovulation cycles, and means for alerting a user to an optimum E3G testing commencement day in the current cycle, said optimum E3G testing commencement day being at least 5 numerical days following the onset of menses in the current cycle but at least 2 numerical days in advance of said earliest numerical day on which actual ovulation occurred.

7. A kit for monitoring the human ovulation cycle, comprising means for initiating the recording of a cycle, means for measuring and recording urinary E3G concentration, means for determining a threshold urinary E3G concentration from measurements taken during the infertile and transition phases of at least one preceding cycle, and means for alerting a user if a measured urinary E3G concentration during the pre-fertile phase of a current cycle exceeds the determined threshold, means for measuring and recording urinary LH and/or P3G concentration, means for determining from such LH and/or P3G concentration the earliest numerical day on which actual ovulation occurred in one or more previous ovulation cycles, and means for alerting a user to an optimum E3G testing commencement day in the current cycle, said optimum E3G testing commencement day being at least 5 numerical davs following the onset of menses in the current cycle but at least 2 numerical days in advance of said earliest numerical day on which actual ovulation occurred and at least one testing device capable of being used to measure urinary E3G concentration and LH concentration.

8. A device for monitoring the human ovulation cycle, comprising a device according to claim 6 together with at least one testing device capable of being used to measure urinary E3G concentration and P3G concentration.

9. A device according to claim 7, comprising a plurality of said testing devices each disposable after individual use.

10. A device according to claim 6 plurality of disposable urinary analyte testing devices, and instructions for use in conjunction with said monitoring device.

11. A test kit according to claim 2, wherein means b) and c) comprise electronic means.

12. A device according to claim 8, comprising a plurality of said testing device each disposable after individual use.

13. A test kit for conducting a method of monitoring the status of a current ovulation cycle of an individual mammalian female subject, involving repeated testing of the body fluid concentration of at least one analyte of significance in relation to the status of the ovulation cycle during at least the pre-ovulation phase of the current ovulation cycle of the individual subject, comprising:

a) one or more testing devices for determining the concentration of said at least one analyte in said body fluid, b) means enabling a user to derive from said concentration an indication of fertility status in the current ovulation cycle by reference to a concentration reference value determined from one or more previous ovulation cycles in the same subject; and c) means enabling a user to derive a precise testing commencement day from knowledge of the numerical day on which actual ovulation occurred during at least one previous ovulation cycle in the same subject.

* * * * *